United States Patent
Zhang et al.

(10) Patent No.: US 9,521,988 B2
(45) Date of Patent: Dec. 20, 2016

(54) VESSEL TREE TRACKING IN ANGIOGRAPHY VIDEOS

(71) Applicant: Siemens Aktiengesellschaft, Munich (DE)

(72) Inventors: Dong Zhang, Orlando, FL (US);
Shanhui Sun, Plainsboro, NJ (US);
Ziyan Wu, Plainsboro, NJ (US);
Bor-Jeng Chen, Los Angeles, CA (US);
Andreas Meyer, Bubenreuth (DE);
Terrence Chen, Princeton, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 14/669,428

(22) Filed: Mar. 26, 2015

(65) Prior Publication Data

US 2016/0235388 A1 Aug. 18, 2016

Related U.S. Application Data

(60) Provisional application No. 62/116,952, filed on Feb. 17, 2015.

(51) Int. Cl.
*A61B 6/00* (2006.01)
*G06T 7/20* (2006.01)
*G06T 11/20* (2006.01)

(52) U.S. Cl.
CPC ............. *A61B 6/547* (2013.01); *G06T 7/2033* (2013.01); *G06T 11/206* (2013.01); *G06T 2207/10016* (2013.01); *G06T 2207/10121* (2013.01); *G06T 2207/20072* (2013.01); *G06T 2207/30101* (2013.01)

(58) Field of Classification Search
CPC ............ G06T 2207/30101; G06T 2207/10081; G06T 2207/20072; G06T 7/0093; G06T 2207/10121; G06T 7/2033; G06T 11/206; G06T 2207/10016; A61B 6/547
See application file for complete search history.

(56) References Cited

U.S. PATENT DOCUMENTS

| | | | |
|---|---|---|---|
| 2005/0203385 A1* | 9/2005 | Sundar | G06T 7/0028 600/427 |
| 2014/0301618 A1* | 10/2014 | Popovic | A61B 1/00009 382/128 |

* cited by examiner

*Primary Examiner* — Vu Le
*Assistant Examiner* — Kenny Cese

(57) ABSTRACT

A method for tracking vessels in image data includes receiving a plurality of image frames and annotating a target vessel in the plurality of image frames. A plurality of tracking targets associated with the target vessel is selected based on a first image frame included in the plurality of image frames. For each respective image frame, a set of tracking points are determined according to a tracking algorithm which includes: selecting a plurality of landmark hypothesis points for each tracking target in the respective frame based on a comparison with a previous image frame, constructing a directed acyclic graph from the plurality of landmark hypothesis points, and solving the directed acyclic graph to yield a plurality of optimal landmarks for the respective image frame.

15 Claims, 14 Drawing Sheets

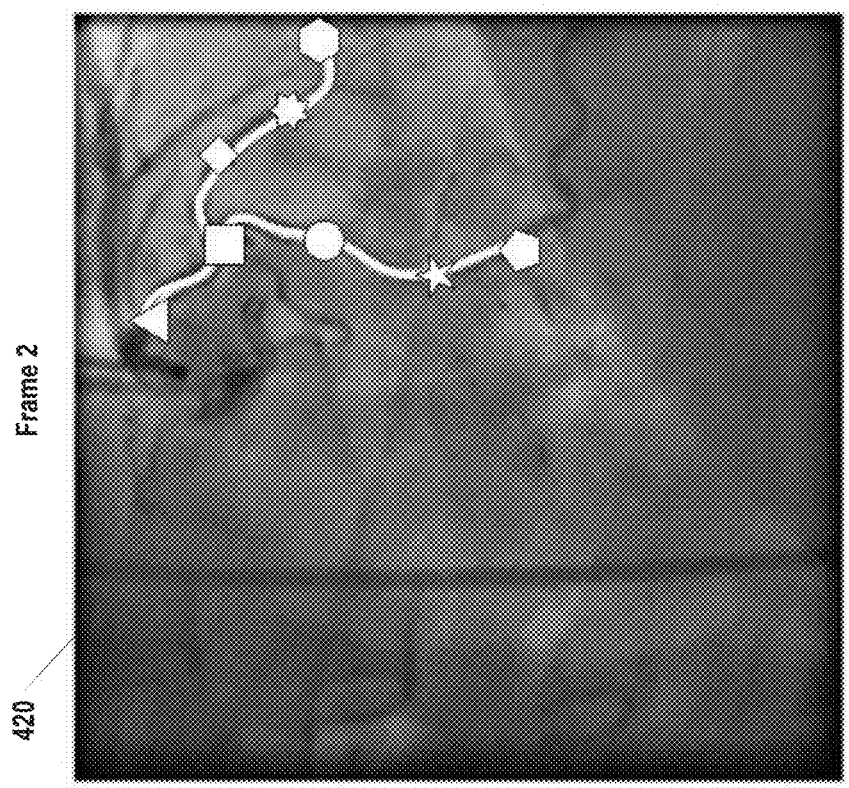
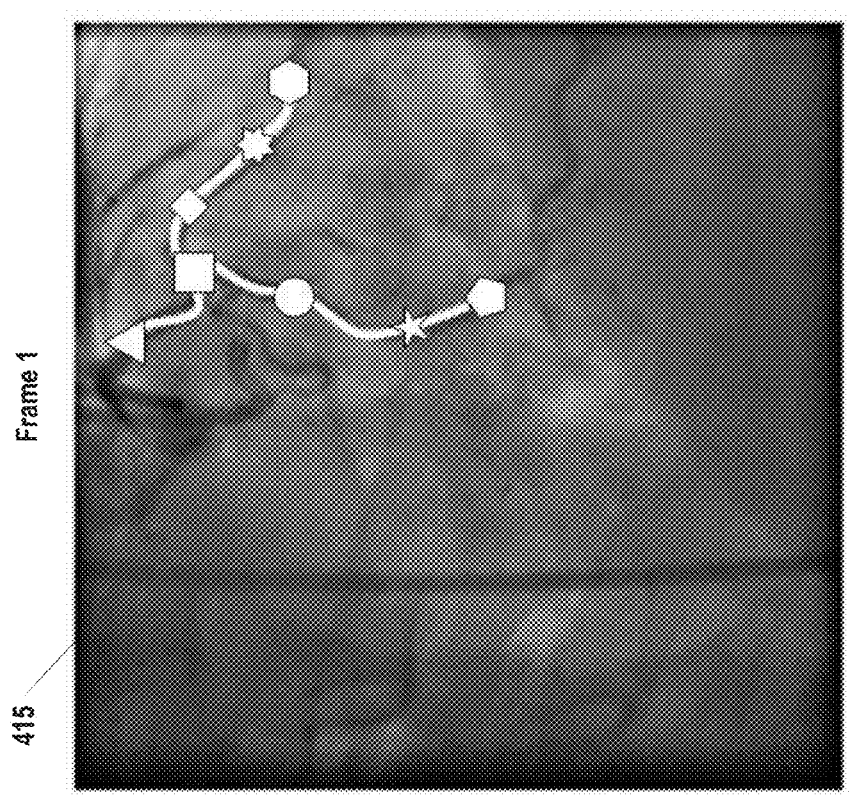
Fig. 4B

VESSEL TREE TRACKING IN ANGIOGRAPHY VIDEOS

CROSS REFERENCE TO RELATED APPLICATIONS

This application claims priority to U.S. provisional application Ser. No. 62/116,952, filed Feb. 17, 2015, which is incorporated herein by reference in its entirety.

TECHNICAL FIELD

The present disclosure relates generally to methods, systems, and apparatuses for performing for the tracking of vessels in video data. The proposed technology may be applied, for example, to vessel tracking in angiography applications.

BACKGROUND

Coronary artery chronic total occlusion (CTO) is a heart disease that causes a decrease in the blood flow of concerned patients. A coronary obstruction is considered a CTO if: 1) it causes a complete blockage of a coronary artery, 2) the duration is more than 3 months, and 3) it has a clinically significant decrease in blood flow. Percutaneous coronary intervention (PCI) is one of the most effective procedures to treat this disease.

During the surgery procedure, surgeons need to track the progress of the catheter in the arteries and insert the guidewire around the blockage of the target vessel in order to further operate (e.g., stent placement) via real-time fluoroscopy imaging (e.g., X-Ray). However, tracking is challenging because the vessels are not visible in the fluoroscopy images without injecting dye (i.e., a contrast agent) into the target vessel. Dye is harmful to the patient and injection needs to be minimized. In a clinical case, usually surgeons inject minimal dye dose to one artery and watch the vessel tree and locate the target vessel. The dye dose keeps the vessel visible for a couple of seconds. This process is called Cine stage and the resulting images with dye injection are referred to as angiography images.

A Cine video is recorded and used for guiding CTO PCI. However, due to the breathing and cardiac motion, the target vessel is moving. Therefore, surgeons have to estimate vessel location in the fluoroscopy images utilizing recorded Cine images and guess during the process of CTO wire insertion. Due to coronary vessel tree's complexity (e.g., potentially including many branches), experienced surgeons may even need to attempt many times to reach the target vessel. This process may take hours and dye needs to be injected many times to help surgeon keep track of the relationship between CTO wire and target vessel. Additionally, it should be noted that the fluoroscopy imaging used during the procedure is also harmful to the patient. Thus, it is desired to provide vessel tracking techniques which minimize the time required during surgical operations.

SUMMARY

Embodiments of the present invention address and overcome one or more of the above shortcomings and drawbacks, by providing methods, systems, and apparatuses related to vessel tracking in video data. More specifically, in various embodiments described herein, the tracking problem is formulated into selecting "optimal" corresponding hypotheses for vessel landmarks which represent the vessel shape obtained from previous frame. Hypotheses selection is formulated as an optimal graph search problem. The results of the graph search are used to track the location of the vessel (or vessel tree) over time and, in some embodiments, a graphical indication of the vessel is overlaid onto an existing image to show the predicted location of the vessel. Thus, a surgical team can track the vessel over a series of images, even in the absence of a contrast agent.

According to some embodiments, a method for tracking vessels in image data includes receiving image frames such as, for example, 2D fluoroscopy images from an X-Ray imaging device. A target vessel is annotated in those image frames (e.g., based on user input or using an automated vessel segmentation process). Tracking targets associated with the target vessel are selected based on a first image frame included in the image frames. For each respective image frame, a set of tracking points are determined according to a tracking algorithm comprising selecting landmark hypothesis points for each tracking target in the respective frame based on a comparison with a previous image frame, constructing a directed acyclic graph from the landmark hypothesis points, and solving the directed acyclic graph to yield optimal landmarks for the respective image frame. In some embodiments, a presentation process is also performed wherein each respective image frame is presented on a display with a visual indication of the target vessel (e.g., a colored line) is overlaid on each respective image frame based on the optimal landmarks associated with that respective image frame.

In some embodiments of the aforementioned method for tracking vessels in image data, the landmark hypothesis points for each tracking target in the respective image frame are determined by performing a similarity matching process with the previous image frame. Techniques such as scoring may be applied to the graph for the purposes of determining similarity. For example, in some embodiments, as part of the similarity process, a unary score may be generated for each node in the directed acyclic graph based on data from the respective image frame and the previous image frame. This unary score may be based on, for example, one or more of local intensity similarity, Frangi vesselness response, and a location constraint. In some embodiments, the unary score of each node may also be adjusted based on points corresponding to the location of a guidewire.

According to other embodiments, an alternative method for tracking vessels in image data includes selecting landmark hypothesis points corresponding to a target vessel included in an image frame. In some embodiments where the image frame is included in a Cine video, the landmark hypothesis points are selected based on a comparison of the image frame and an immediately preceding imaging frame in the Cine video. A graph (e.g., a directed acyclic graph) is constructed where each node of the graph corresponds to the one or more landmark hypothesis points. The graph is solved to identify optimal landmarks corresponding to the target vessel. A graphical indication of the target vessel is generated based on the optimal landmarks and the image frame is presented on display with the graphical indication of the target vessel overlaying the image frame.

In some embodiments of the aforementioned alternative method for tracking vessels in image data, scoring is applied to the graph. For example, in one embodiment, a unary score is determined for each of the nodes based on the comparison of the image frame and the immediately preceding imaging frame in the Cine video. The graph may then be solved based on the unary score determined for each of the nodes. Additionally (or alternatively) in some embodiments, the landmark hypothesis points corresponding to the target vessel included in the image frame are selected based on the unary score determined for each of the nodes. In some embodiments, the unary score for each node in the graph may be adjusted based on one or more guidewire points corresponding to a location of a guidewire in the image frame. In addition to the aforementioned unary scores, in some embodiments, a binary score is determined for each graph edge included in the graph. Each respective binary score enforces a structural constraint determined based on the comparison of the image frame and the immediately preceding imaging frame in the Cine video. The graph may then be solved based on the binary score of determined for each of the nodes.

According to other embodiments, a system for tracking vessels in image data comprises an imaging computer and a display. In some embodiments, this system also includes an X-Ray imaging device configured to acquire the image data. The imaging computer in the aforementioned system is configured to execute components comprising an annotation component, a landmark selection component, a graph construction component, and a graph solving component. The annotation component is configured to annotate a target vessel in image frames. The landmark selection component is configured to select tracking targets associated with the target vessel based on a first frame included in the image frames. The hypothesis generation component is configured to select landmark hypothesis points for each tracking target in the image frames. In some embodiments, the imaging computer is further configured to execute a guidewire tracking component configured to track a location of a guidewire. The landmark hypothesis points may then be selected based on the location of the guidewire related to the target vessel. The graph construction component is configured to construct a directed acyclic graph from the landmark hypothesis points. The graph solving component is configured to solve the directed acyclic graph to yield optimal landmarks for each respective image frame in the image frames.

The display in the aforementioned system is configured to present each respective image frame included in the image frames, and overlay a visual indication of the target vessel on each respective image frame in the image frames based on the optimal landmarks associated with the respective image frame.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures:

FIG. 4B shows images indicating curves with keypoints which formulate the targets for vessel tracking, according to some embodiments;

DETAILED DESCRIPTION

The following disclosure describes several embodiments directed at methods, systems, and apparatuses related to vessel tracking in video data. More specifically, in various embodiments described herein, the tracking problem is formulated into selecting "optimal" corresponding hypotheses for vessel landmarks which represent the vessel shape obtained from previous frame. To this end, the "optimal" hypotheses selection problem is transformed into an optimal graph search problem. In some embodiments, a Directed Acyclic Graph (DAG) is developed to incorporate both appearance and shape information in the graph construction. To make the vessel tracking more robust, additional guidewire tracking information may be utilized to constrain appearance based score. This graph based optimization problem is solved in some embodiments by an efficient dynamic programming algorithm. The techniques described herein may be applied, for example, to tracking vessel tree in 2D X-Ray angiography videos. Additionally, various embodiments described herein are suitable for tracking target vessel in coronary artery chronic total occlusion (CTO) cases. Thus, the disclosed techniques may be used in, for example, prediction based CTO Percutaneous Coronary Intervention (PCI) guidance applications. Moreover, the disclosed vessel tree tracking techniques can have other applications including, without limitation, the analysis of vascular tree structure, learning heart motion from tracking vessel motion, 3D vessel tree reconstruction from tree structure of motion, etc.

Figure 1:
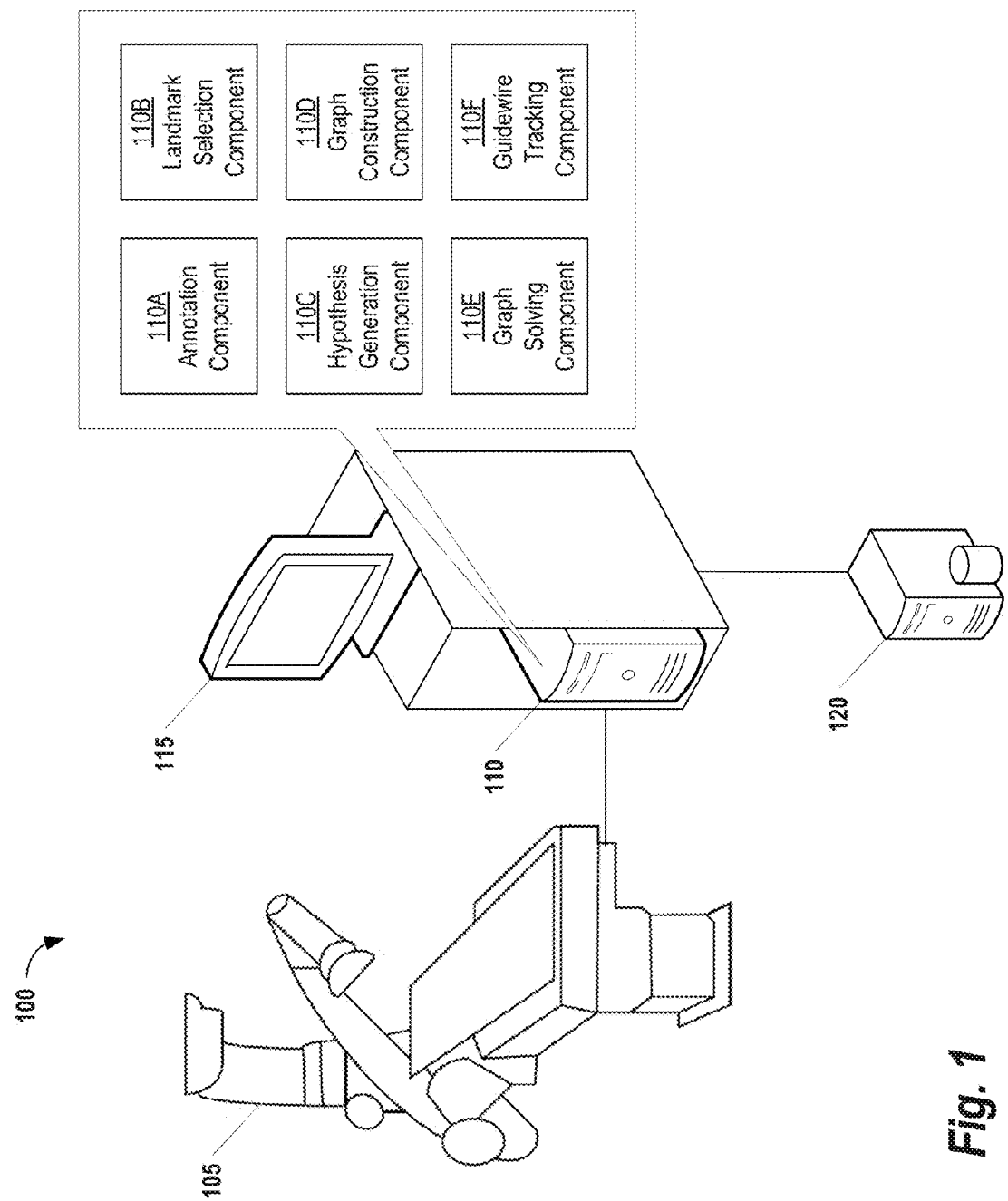
FIG. 1 provides an overview of a system for vessel tracking, according to some embodiments.

FIG. 1 provides an overview of a system 100 for vessel tracking, according to some embodiments. The system 100 may be used, for example, in Angiography (catheterization and stent manipulation) or other medical procedure to enhance vessel visualization and tracking. Briefly, the system 100 includes an X-ray Imaging Device 105 which is operably coupled to an Imaging Computer 110 and Display 115. In some embodiments, the system 100 also includes a Remote Database Server 120. X-ray Imaging Device 105 gathers imaging data which is processed by Imaging Computer 110 and then stored, either on the Imaging Computer 110 or on the Remote Database Server 120. During surgical procedures, the imaging data is retrieved by the Imaging Computer 110 for presentation on a Display 115. It should be noted that, while imaging device in FIG. 1 is an x-ray device, other imaging modalities may be used in different embodiments including, without limitation, Computed Tomography and Magnetic Resonance Imaging devices.

The system 100 acquires, during a medical procedure, data representing multiple temporally sequential individual images of vessels of a portion of patient anatomy using X-ray Imaging Device 105. X-ray Imaging Device 105 comprises a C-arm X-ray radiation source and detector device rotating about a patient table and an associated electrical generator for providing electrical power for the X-ray radiation system. The sequential individual images encompass introduction of a contrast agent (or interventional device).

Imaging Computer 110 includes an interface which receives a signal from X-ray Imaging Device 105 indicating X-ray radiation dosage for performing imaging is substantially stable. Imaging Computer 110 automatically processes data representing multiple temporally sequential individual images of a portion of patient anatomy to identify first and second images. The first image comprises an image in the multiple temporally sequential individual images determined in response to the received signal. The second image is substantially exclusive of an indication of presence of a contrast agent successively followed by an image indicating presence of a contrast agent and is identified by comparing a difference between measures representative of luminance content of the second image and the image indicating presence of a contrast agent, with a threshold. An imaging controller in the Imaging Computer 110 controls operation of X-ray Imaging Device 105 in response to user commands entered via a user interface (not shown in FIG. 1).

Although FIG. 1 only illustrates a single imaging computer 110, in other embodiments, multiple imaging computers may be used. Collectively, the one or more imaging computers provide functionality for viewing, manipulating, communicating and storing medical images on computer readable media. Example implementations of computers that may be used as the imaging computer 110 are described below with reference to FIG. 12.

At least one data repository stores medical image studies for multiple patients in Digital Imaging and Communications in MediCine (DICOM) compatible (or other) data format. In some embodiments, this repository is on the Imaging Computer 110, while in other embodiments, a Remote Database Server 120 may be used as the repository. A medical image study individually includes multiple image series of a patient's anatomical portion which in turn individually includes multiple images. When imaging data is needed (e.g., during a surgical procedure), Imaging Computer 110 retrieves the imaging data from the database (either at Imaging Computer 110 or Remote Database 120) for presentation on a Display 115 to help guide the surgical team performing the operation. Alternatively, the Imaging Computer 110 may immediately present the received imaging data upon receipt from the Imaging Computer 110.

In addition to the functionality described above, the Imaging Computer 110 may be configured to track vessel tree information in the imaging data acquired from the X-ray Imaging Device 105. The vessel branch is represented by a curve. At the first frame of interest, an Annotation Component 110A annotates the target vessel. In some embodiments, this annotation is performed based on user-based inputs (e.g., interaction with a GUI displaying one or more images). In other embodiments, an automated (or semi-automated) vessel segmentation technique known in the art may be used. This vessel segmentation technique may include, for example, a pattern recognition, model-based tracking and propagation, neural network, fuzzy, and artificial intelligence-based technique.

A Landmark Selection Component 110B selects tracking targets (keypoints) from the curve on the first image frame. A Hypothesis Generation Component 110C generates N hypotheses for each landmark in the current frame based on similarity matching between current frame and previous frame. Then, an optimal set of landmarks is determined to form the tracked vessel. This optimal landmark selection is formulated as an optimal graph search problem. To approach this, a Graph Construction Component 110D constructs a directed acyclic graph (DAG) from landmark hypotheses. Then, a Graph Solving Component 110E solves the constructed graph using, for example, one or more dynamic programming techniques known in the art. In some embodiments, a Guidewire Tracking Component 110F provides guidewire tracking to support the vessel tracking algorithm. The utilized support information makes the CTO target vessel tracking more robust. However, it should be noted that guidewire tracking is optional based on different applications.

Based on the results of this search problem, vessel location can be determined and a graphical indication of the vessel may be overlaid on the images presented on Display 115 during the surgical procedure. For example, in some embodiments, a solid, colored line is generated and overlaid over the vessel on the Display 115. As described in further detail below, modeling techniques may be applied to compensate for motion of the vessel over time. Thus, the graphical indication may move over time such that it is always over the predicted location of the vessel structure.

Figure 2A:
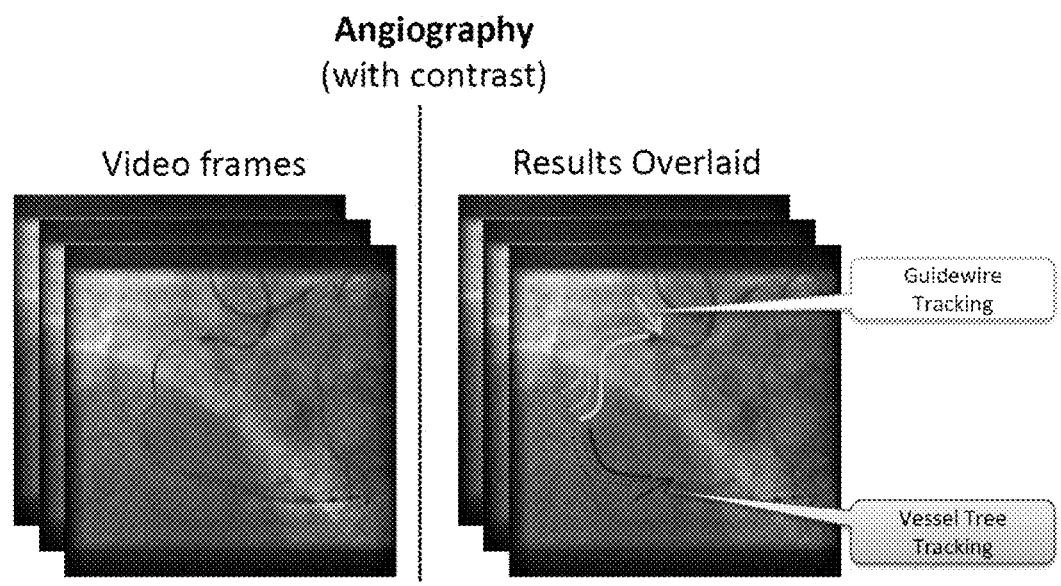
FIG. 2A provides an overview of prediction-based CTO PCI guidance framework in angiography, according to some embodiments.
Figure 2B:
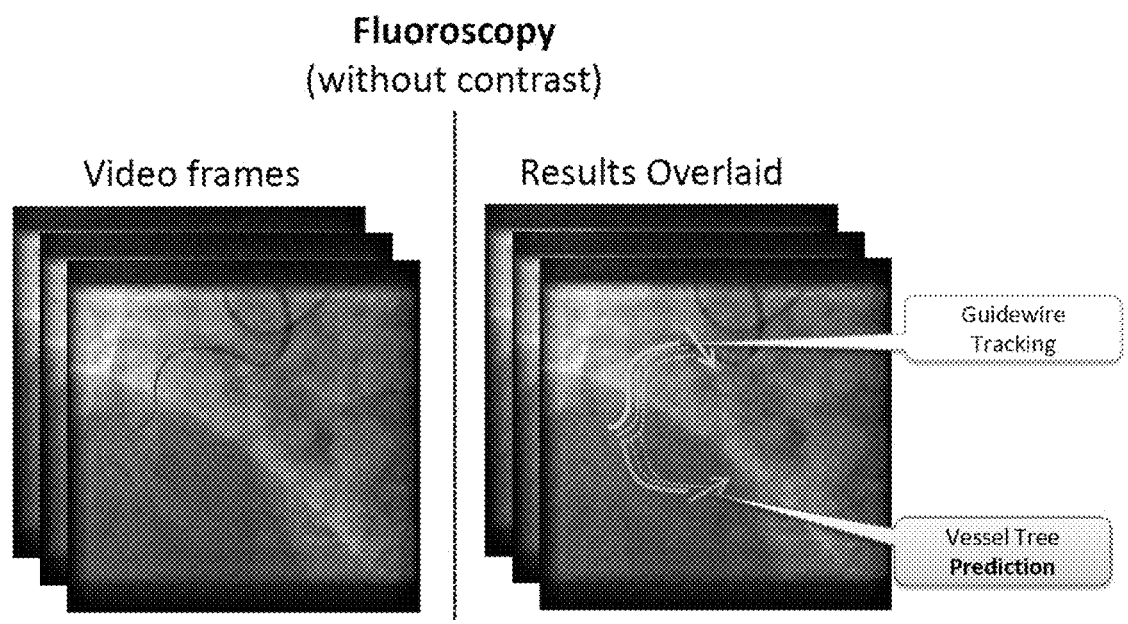
FIG. 2B provides an overview of prediction-based CTO PCI guidance framework in fluoroscopy, according to some embodiments.

FIGS. 2A and 2B provides an overview of prediction-based CTO PCI guidance framework in both angiography (FIG. 2A) and fluoroscopy (FIG. 2B), according to some embodiments. More specifically, these figures share a framework to predict CTO target vessel in the real-time fluoroscopy utilizing learnt guidewire and vessel motion model from angiography and tracked guidewire information in fluoroscopy. This framework is feasible to guide CTO PCI. In conventional systems, the target vessel in the Cine video is manually annotated. However, the manual annotation is time consuming and impractical in a clinical application. Therefore, an automated vessel tracking algorithm, is described in further detail below.

Figure 3:
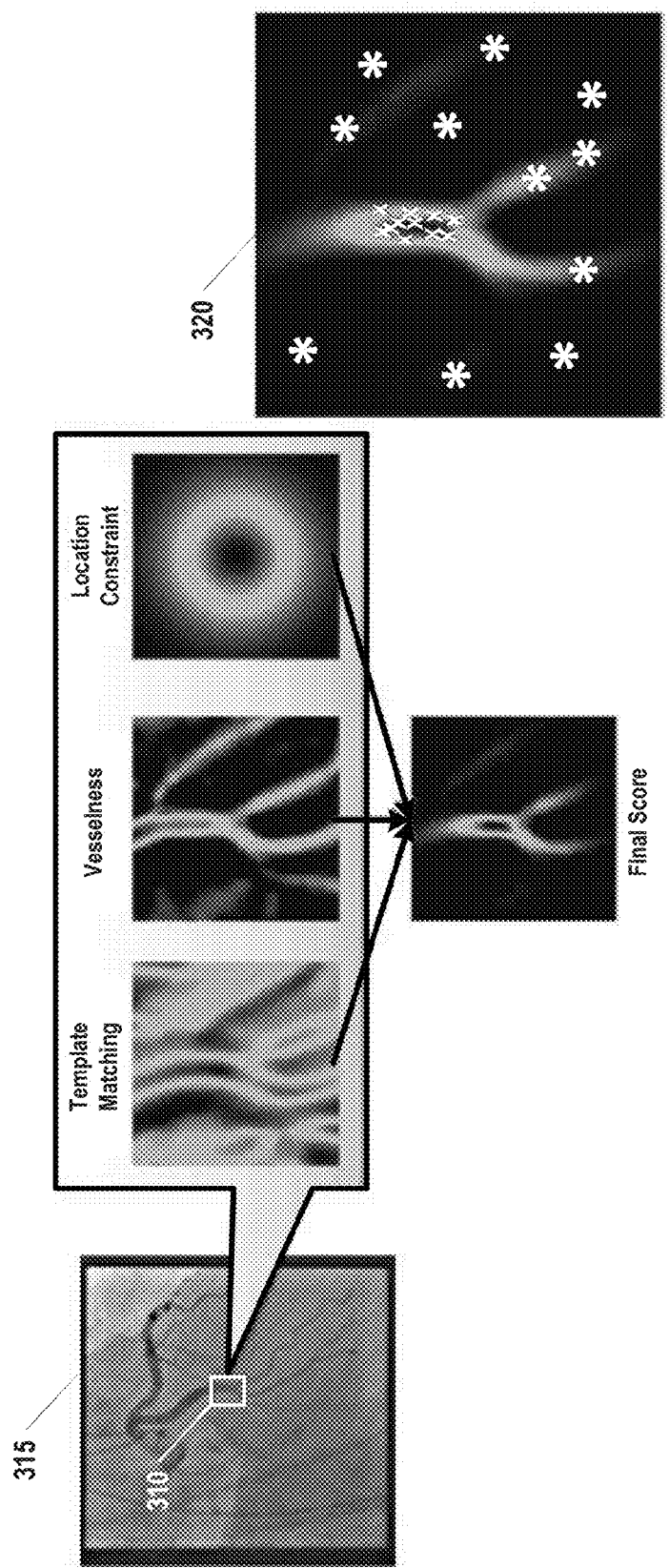
FIG. 3 provides of feature map generation and top N hypotheses of a landmark selection, according to some embodiments.

FIG. 3 provides of feature map generation and top N hypotheses of a landmark selection, according to some embodiments. As shown on the left-hand side of FIG. 3, the feature map used for unary score is a fusion of a template matching, vesselness map and a location constraint map. The white square 310 in the X-ray image 315 indicates the template matching window. The image 320 on the right hand side of FIG. 3 shows that N hypotheses comprise global maxima (white 'x') and local maxima (white '*') of the feature map.

Figure 4A:
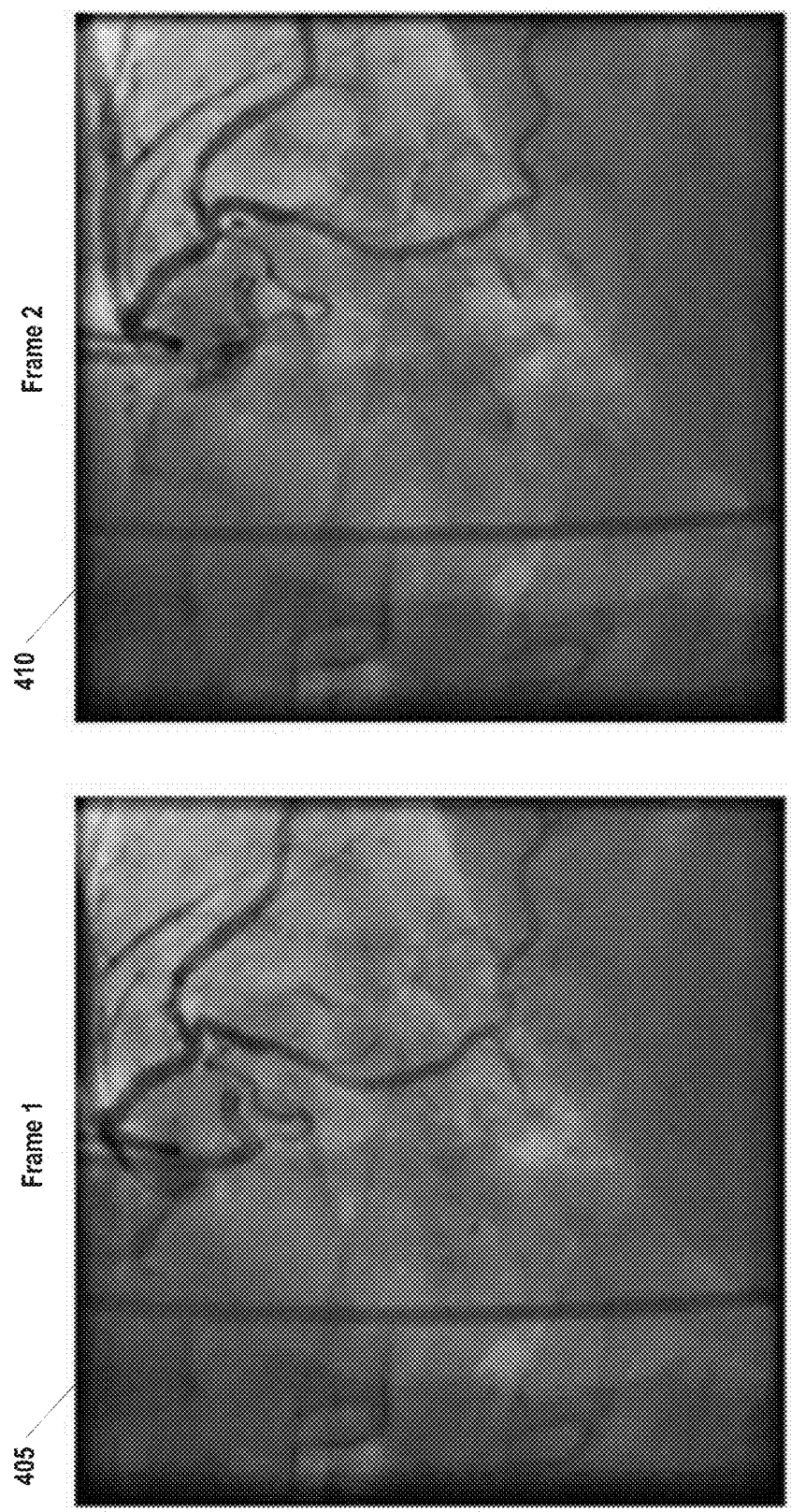
FIG. 4A indicates two consecutive frames including vessel of interest.
Figure 4C:
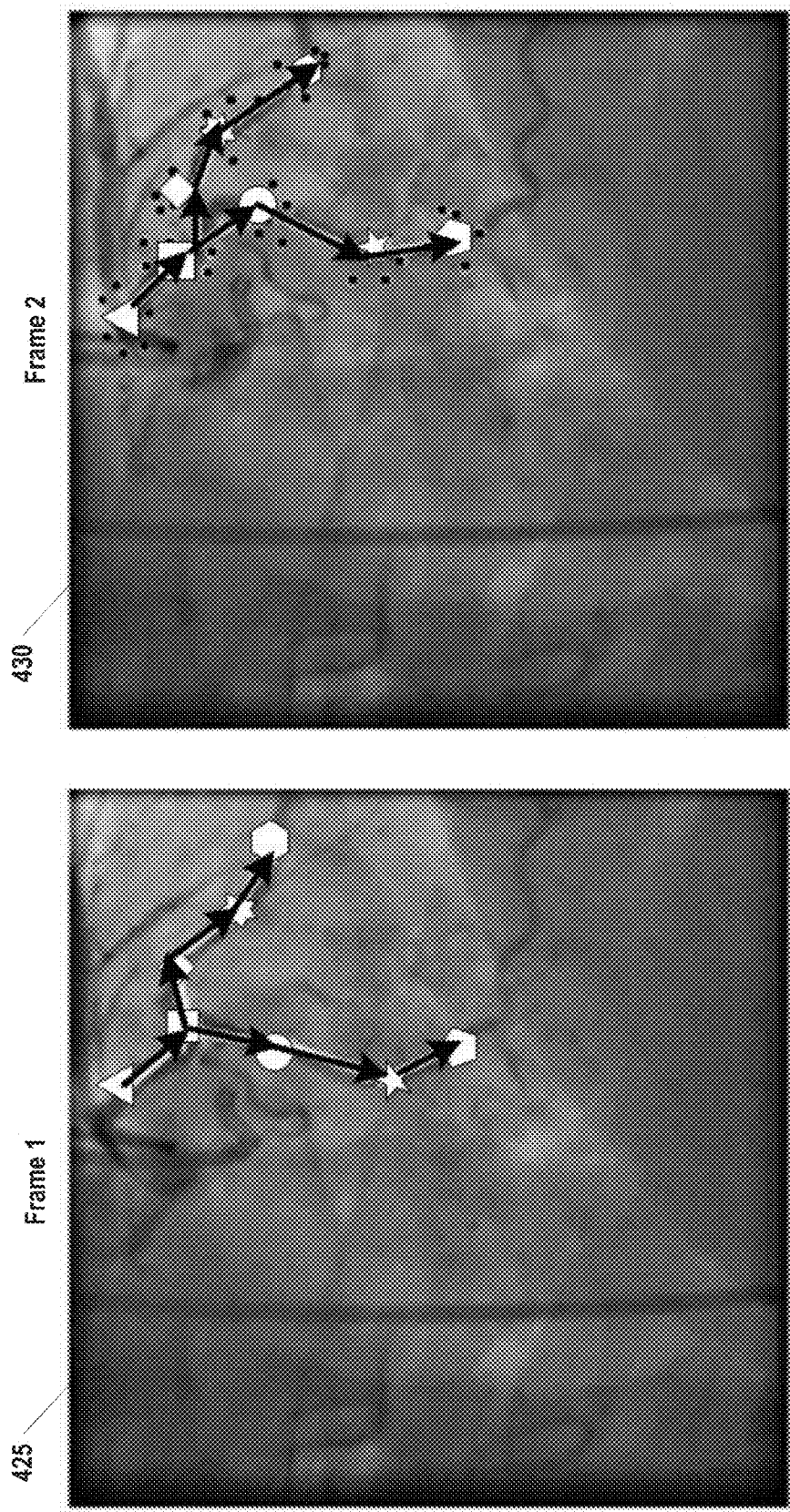
FIG. 4C show images indicating hypotheses generated from corresponding keypoints, according to some embodiments.

FIGS. 4A, 4B, and 4C illustrate various components of used in vessel tracking, according to some of the techniques described herein. FIG. 4A indicates two consecutive frames 405, 410 including vessel of interest. The two images 415, 420 in FIG. 4B indicate curves with keypoints which formulate the targets for tracking. In this example, keypoints are indicated by different shaped icons overlaid on each image. The two images 425, 430 in FIG. 4C indicate hypotheses (image 430) generated from corresponding keypoints (image 425). Coronary vessel trees are non-rigid deformable structures due to breathing and cardiac motion. The vessel branch could be modeled, for example, as BSpline curve controlled by landmarks (FIG. 4B). In the techniques described herein, each landmark is tracked in consecutive frames. Suppose the vessel tree structure in frame f−1 is given, generated for frame f, hypothesis points for each landmark from frame f−1 in certain distance. In various embodiments, described in greater detail below, hypotheses are generated for the local patch around the landmark, according to a unary score map. Briefly, a predetermined number of global maximums (top maximal scores) are selected to be part of the hypotheses (shown as white 'x' in FIG. 3). Next, the patch is divided into equal-size grids and several local maximums are selected to be the rest of the hypotheses (shown as white '*' in FIG. 3)

Figure 5:
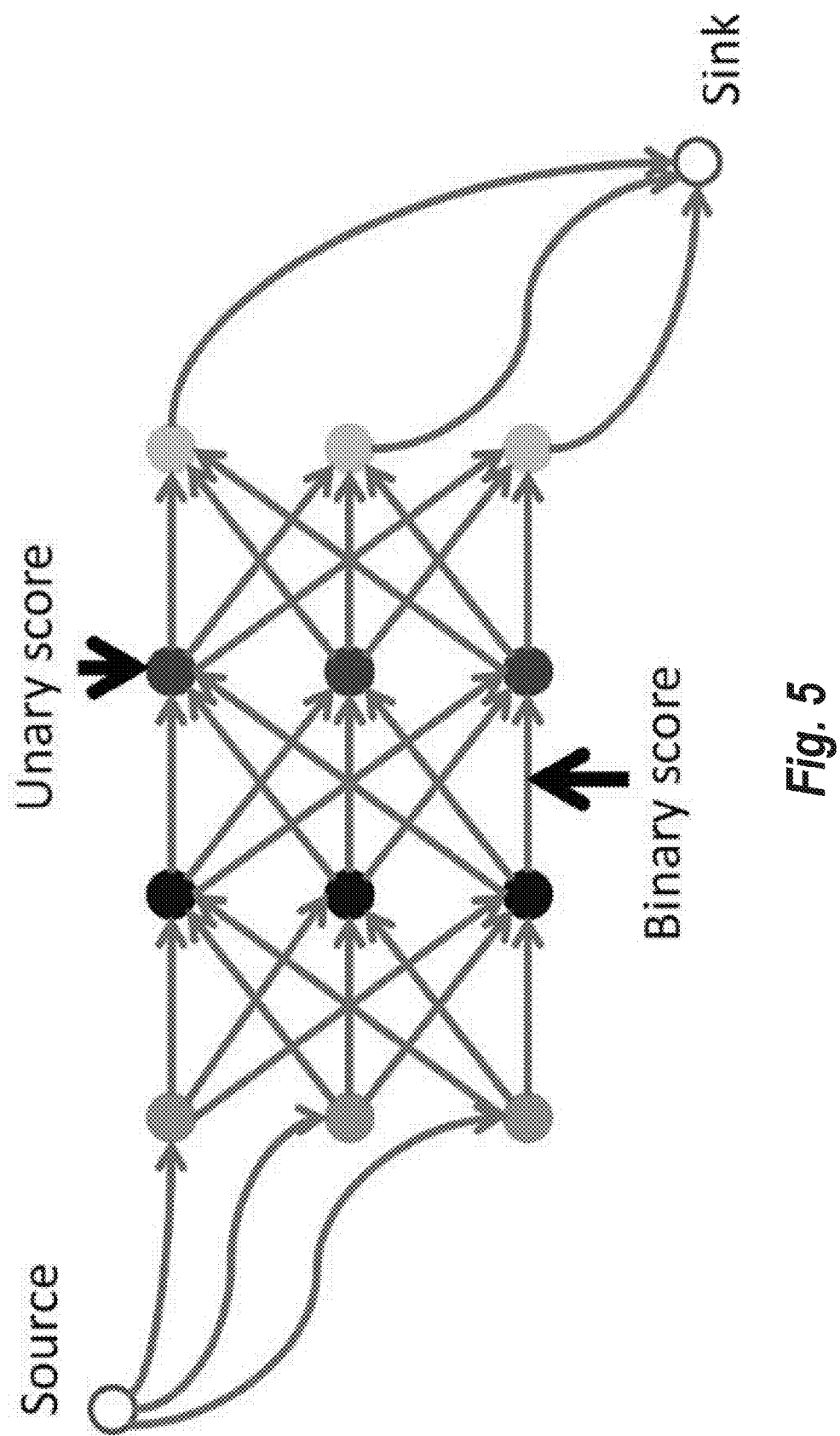
FIG. 5 provides an example of the construction of a directed acyclic graph for use in finding the optimal vessel landmarks on a frame f, as may be implemented in some embodiments.

FIG. 5 provides an example of the construction of a directed acyclic graph for use in finding the optimal vessel landmarks on a frame f, as may be implemented in some embodiments. Each column of the graph in this example represents each vessel keypoint. Column nodes represent hypotheses of the corresponding keypoints. Between neighboring columns, nodes are fully connected by directed edges. Source and sink nodes are added to form a standard graph search problem. More specifically, a vessel tree or vessel branch has L landmarks. Each landmark has N hypotheses. In the graph G=(V, E) where V is graph node set and E is graph edge set, there are L columns and L×N nodes. Graph nodes on neighboring columns are fully connected by directed graph edge.

To represent the appearance similarity of the corresponding landmarks between the frame f and frame f−1, unary scores are assigned to each node in the graph shown in FIG. 5. Binary scores are assigned to graph edge (as described in further detail below). They enforce structural constraint of two adjacent landmarks between the frame f and f−1. Let $U_i^k$ be the unary score of the $k^{th}$ hypothesis (node) of the $i^{th}$ landmark (column), and $B_{ji}^{kl}$ be the binary scores between $k^{th}$ hypothesis of the $i^{th}$ landmark and $l^{th}$ hypothesis of the $j^{th}$ landmark. The objective is to select one graph node for each column such that the energy on the path is maximized. The energy function, for a given path $P=\{p_i\}_{i=1}^{L}$, where $p_i$ is a graph node on the $i^{th}$ column, may be computed as follows:

$$M = \left( \sum_{p_i \in P} U_i^{p_i} + \lambda_B \sum_{p_j, p_i \in P} B_{ji}^{p_j p_i} \right) \quad (1)$$

where $\lambda_B$ is weight parameter, and the optimal solution determined according to the following equation:

$$P^* = \underset{P}{\mathrm{argmax}}\, M. \quad (2)$$

In some embodiments, the unary score for the nodes in the graph are generated based on a local intensity similarity $U_f^{Iy}$, Frangi vesselness response $U_f^{Vs}$ and the location constraint $L_f^{Lo}$ according to the following equation:

$$U_j = \lambda^{Iy} \cdot U_f^{Iy} + \lambda^{Vs} \cdot U_f^{Vs} + \lambda^{Lo} \cdot U_f^{Lo} \quad (3)$$

where $\lambda^{Iy}$, $\lambda^{Vs}$, and $\lambda^{Lo}$ are weights. The value of $U_f^{Iy}$ may be generated as follows:

$$U_f^{Iy}(I_{f-1}, I_f) = \frac{1}{n} \sum_{x,y} \frac{(I_{f-1}(x,y) - \bar{I}_{f-1})(I_f(x,y) - \bar{I}_f)}{\sigma_{I_f} \sigma_{I_{f-1}}} \quad (4)$$

where n is the number of pixels in a matching template patch ($I_f$ and $I_{f-1}$ for frame f and f−1, respectively). $\bar{I}_f$ and $\sigma_{I_f}$ are the mean gray value and standard deviation in the template $I_f$, while $\bar{I}_{f-1}$ and $\sigma_{I_{f-1}}$ are the mean gray value and standard deviation in the template $I_{f-1}$. $U_f^{Lo}$ is a 2D Gaussian function which ensures that points near the center of the search bounding box have higher weights:

$$U_f^{lo} = \frac{1}{\sigma_{lo}\sqrt{2\pi}} \exp\left(-\frac{d^2}{2\sigma_{lo}^2}\right) \quad (5)$$

where d is the distance to the center of a search bounding box and $\sigma_{Io}$ is a standard deviation.

The binary scores may be computed as follows. For two adjacent landmarks in the vessel tree $\hat{v}_i$ and $\hat{v}_j$ on the frame f−1, let $(\hat{v}_i(x), \hat{v}_i(y))$ and $(\hat{v}_j(x), \hat{v}_j(y))$ be the x-y location of the landmarks, and the relative location of i and j is representative as the vector $v_{ij}=(\hat{v}_i(x)-\hat{v}_j(x), \hat{v}_i(y)-\hat{v}_j(y))$. Similarly, the relative location of landmark hypotheses on the frame f is modeled as $v_{ij}^{kl}$ for the landmark i, j and hypotheses k, l. The binary scores between two hypotheses are assigned as $$B_{ji}^{kl} = -\frac{|\|v_{ij}^{kl}\|_2 - \|v_{ij}\|_2|}{\|v_{ij}\|_2} \cdot \frac{|\angle(v_{ij}^{kl}, v_{ij})|}{\pi}, \quad (6)$$

where $\|\bullet\|$ is L2 norm of the vector, $\angle(\bullet,\bullet)$ is the angle ($\in[0, \pi]$) between two vectors.

To find the global optimal solution of the DAG, an efficient dynamic programming process may be used. Let M(i,k) be maximized for $k^{th}$ hypotheses $i^{th}$ landmark. According to Equation 1, the recursive function of dynamic programming is:

$$M(i,k) = \max_{k=1\ldots|V_i|} \left( U_i^k + \sum_{\hat{v}_j \in kids(\hat{v}_i)} (\lambda_B B_{ji}^{lk} + M(j,l)) \right) \quad (7)$$

Since M(i, j) can be obtained recursively, the time complexity of the algorithm is O(LN). The optimal solution could be obtained by backtrack with a complexity of O(L). Therefore, the overall time complexity is linear (with respect to the number of nodes in the graph LN).

Figure 6:
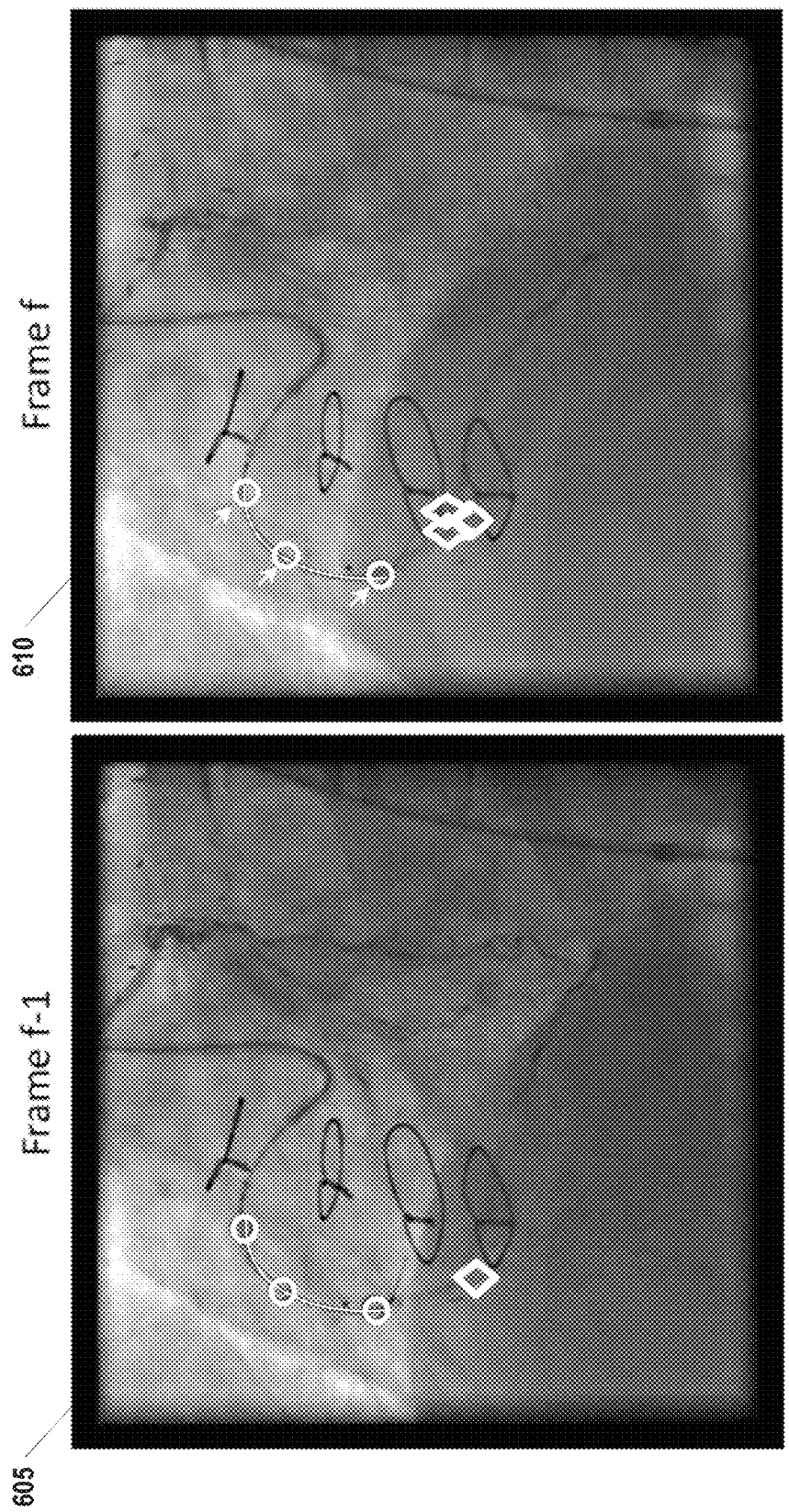
FIG. 6 shows an example of guidewire guided vessel tracking in two image frames, according to some embodiments.

FIG. 6 shows an example of guidewire guided vessel tracking in two image frames 605, 610, according to some embodiments. During CTO PCI, there is a CTO guidewire inserted into the arteries to guide the surgery procedure. The guidewire is visible in X-ray imaging. The guidewire has strong motion correlation with the target vessel. Therefore, the guidewire provides additional clues for vessel tracking and to improve tracking performance. In FIG. 6, the white circles are the keypoints on the guidewire, the white diamond is one of the landmarks of the vessel of interest, and the predicted search region for this landmark is shown in the right image frame 610. As illustrated in FIG. 6, H keypoints are selected on the guidewire on the frame f−1. On the frame f, each such keypoint predicts a location for each vessel landmark as indicated in FIG. 6. Overall, there are H*L predicted locations. A Gaussian distribution based weighting map $W_f(h)$ is then created based on $h^{th}$ predicted location as shown in the following equation:

$$W_f(h) = \frac{1}{\sigma_k \sqrt{2\pi}} \exp\left(-\frac{d_s(h)^2}{2\sigma_k^2}\right) \quad (8)$$

where h is $h^{th}$ predicted location, ds is a pixel distance to $h^{th}$ predicted location, and $\sigma_k$ is a standard deviation. The overall weighting map $W_f$ may then be defined as follows:

$$W_f = \frac{\sum_{h=1}^{H*L}(W_f(h))}{\max_{h=1}^{H*L}(W_f(h))} \quad (9)$$

The weighting map may then be utilized to adjust the unary score map $U_f$ as follows:

$$U_f = \begin{cases} U_f \odot W_f & \text{use guidewire} \\ U_f & \text{no guidewire} \end{cases} \quad (10)$$

where $\odot$ is a pixel-wise multiplication.

FIGS. 7-11 provide a list of results gathered using test datasets to demonstrate the applicability of the techniques described herein to CTO vessel branch tracking and vessel tree tracking. For these test sets, the weight values of Equation 3 (i.e., $\lambda^{Ty}$, $\lambda^{Vs}$, $\lambda^{Lo}$ and $\lambda_B$) were all set to 1 and the following error metric was utilized to evaluate the tracking performance:

$$d_e = \frac{\text{mean}(d(S, R) + \text{mean}(d(R, S))}{2.0} \quad (11)$$

where d(X, Y) is Euclidean distance of the pixels on the curve X to the curve Y. S is the tracking result and R is the ground truth.

Figure 7:
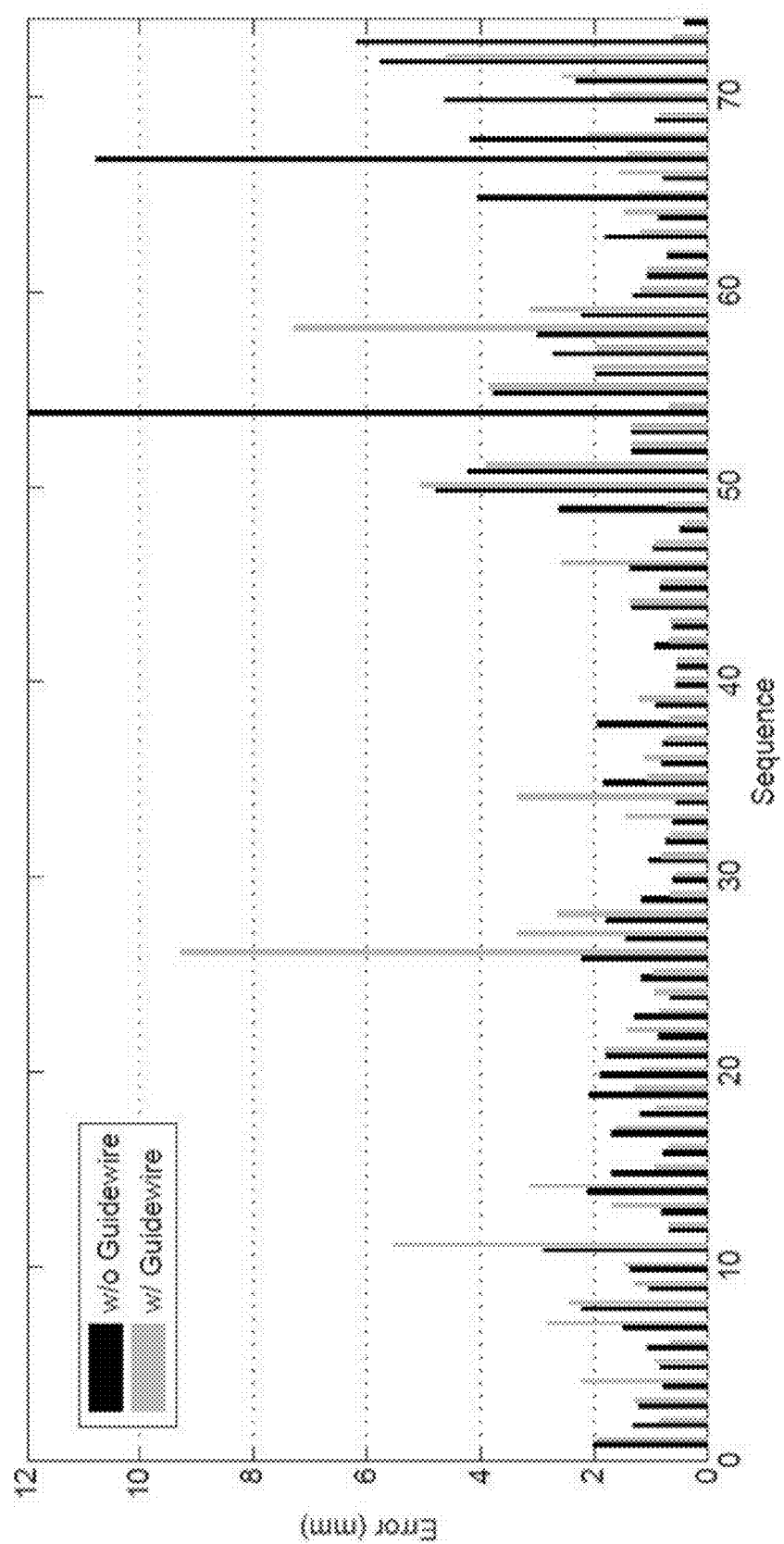
FIG. 7 provides the results (per case) of CTO Cine videos, as generated according to some embodiments.
Figure 8:
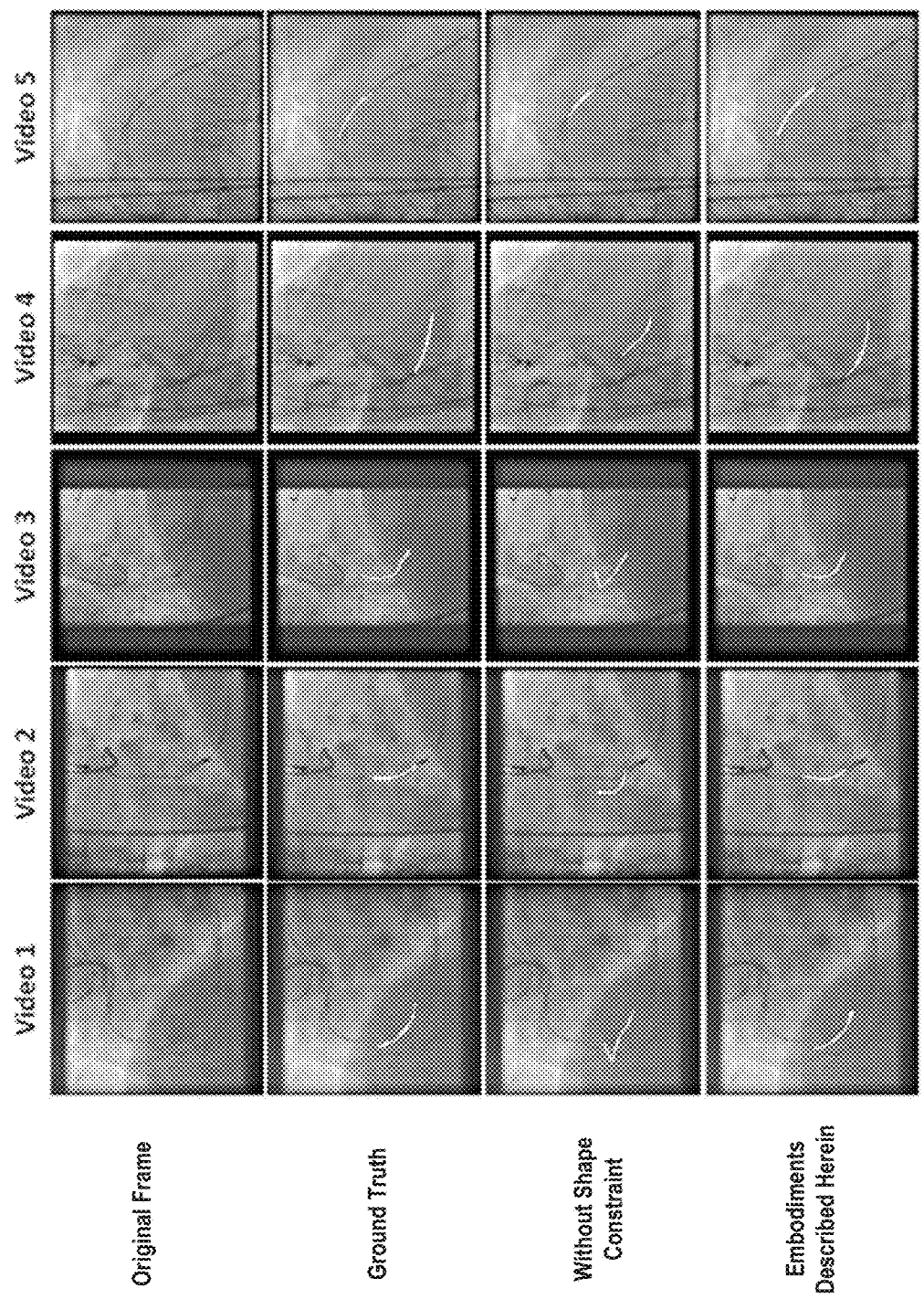
FIG. 8 provides examples and comparison of results for CTO target vessel tracking where a solid white line is used to show the location of the vessel branch, according to some embodiments.

To illustrate the techniques described herein for CTO target vessel branch tracking applications, 74 CTO Cine videos were used for evaluation. The frame size is either 512×512 or 600×600 pixels and the size of the pixels is about 0.25 mm (with min: 0.184 mm and max: 0.368 mm). Vessel branches of clinical interest were annotated frame by frame as ground truth by an expert. FIG. 7 provides the results (per case) of CTO Cine videos, as generated according to some embodiments. The distance error is 1.95±2.02 (mean±standard deviation) mm without guidewire guidance, and 1.74±1.57 mm with guidewire guidance. FIG. 8 illustrates example results. More specifically, FIG. 8 provides examples and comparison of results for CTO target vessel tracking where a solid white line is used to show the location of the vessel branch, according to some embodiments. In this example, the first row shows the original images included in the video data. The second row shows the ground truth of the images. The third row is the tracking result without enforcing shape constraint (i.e., no binary edge term in Equation 1). The fourth row is the result generated according to the techniques described herein.

Figure 9:
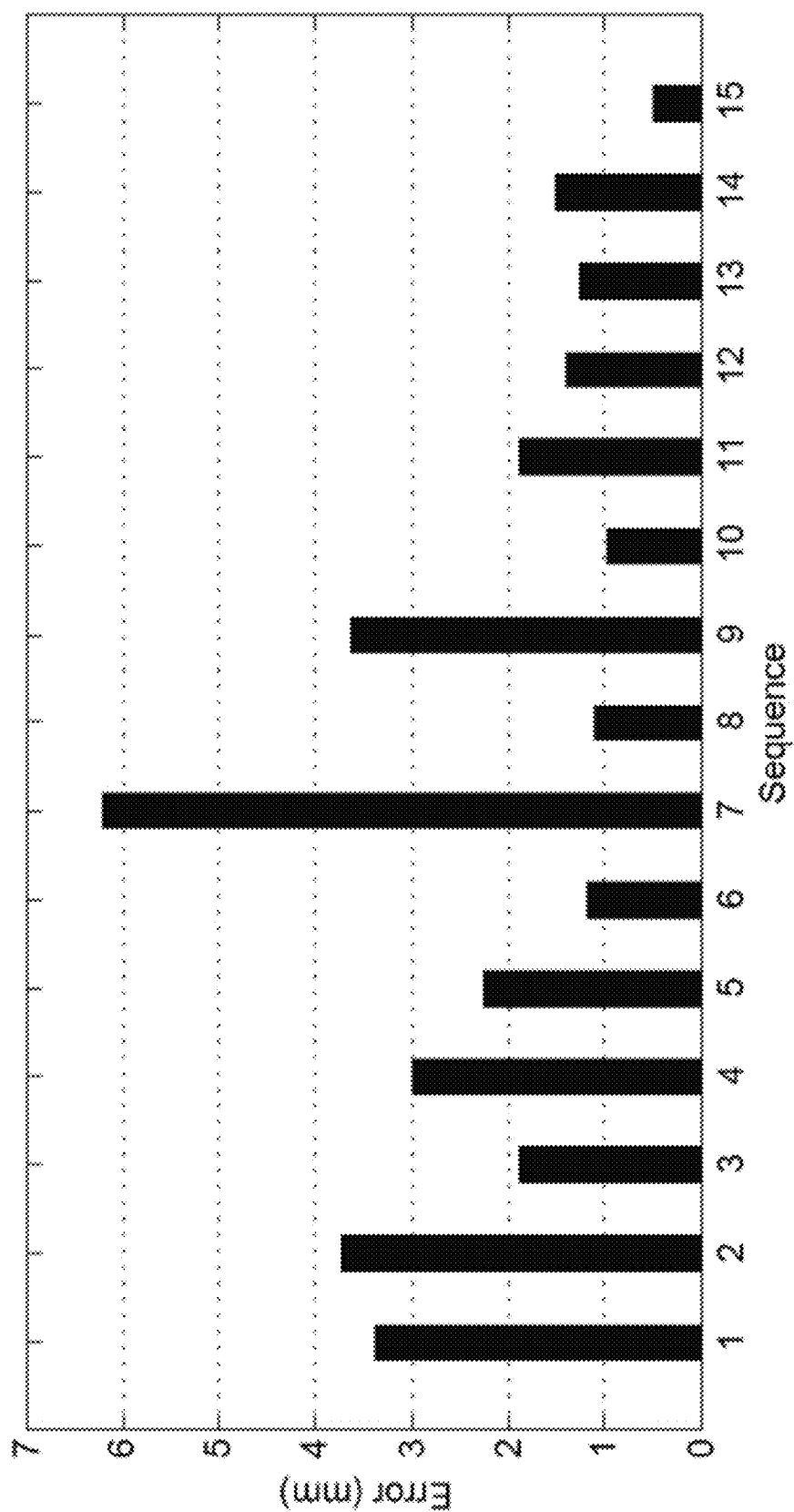
FIG. 9 shows quantitative results (per case) of vessel tree dataset, as generated according to some embodiments.
Figure 10:
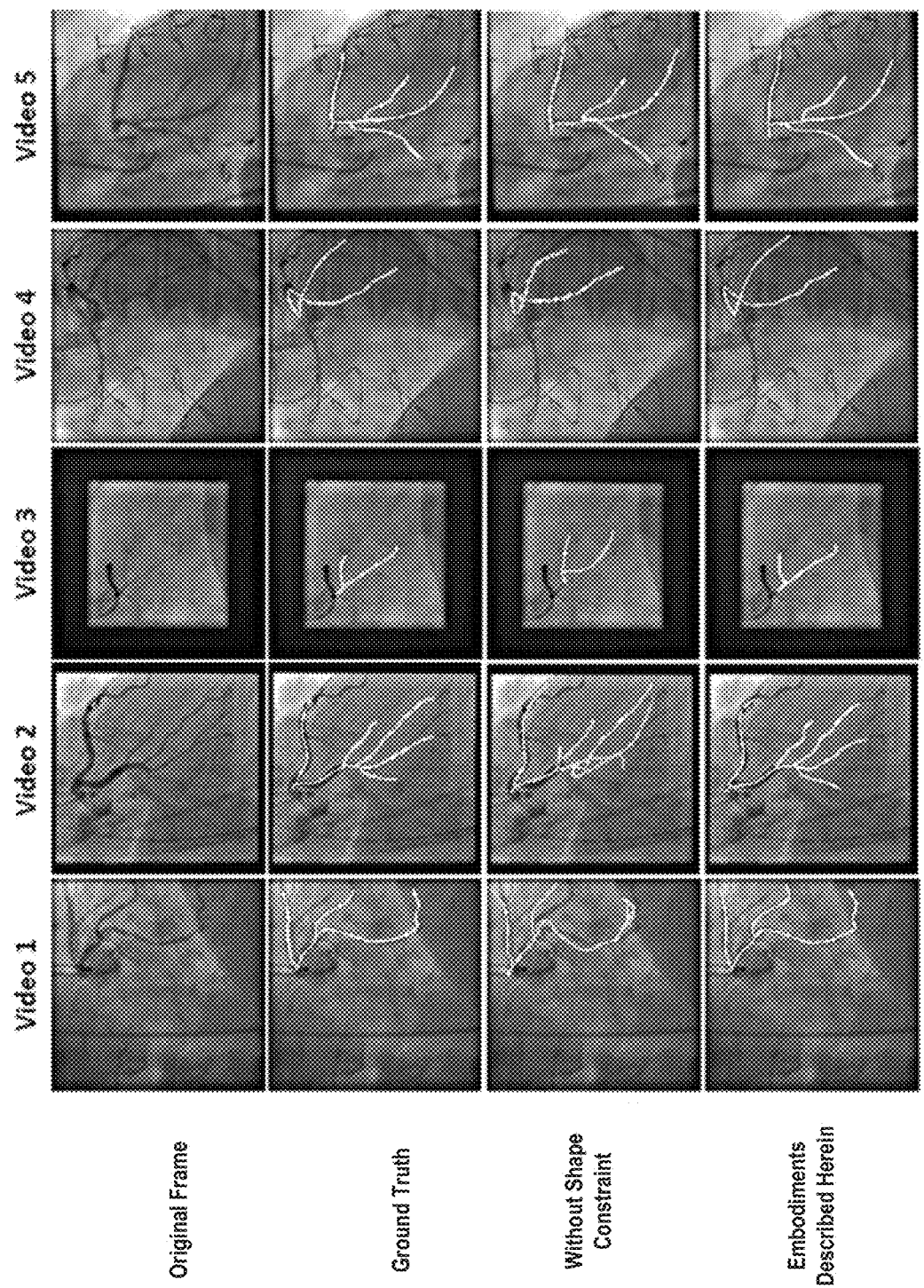
FIG. 10, provides examples and comparison of results for vessel tree tracking where a solid white line is used to show the location of the vessel tree, according to some embodiments.
Figure 11:
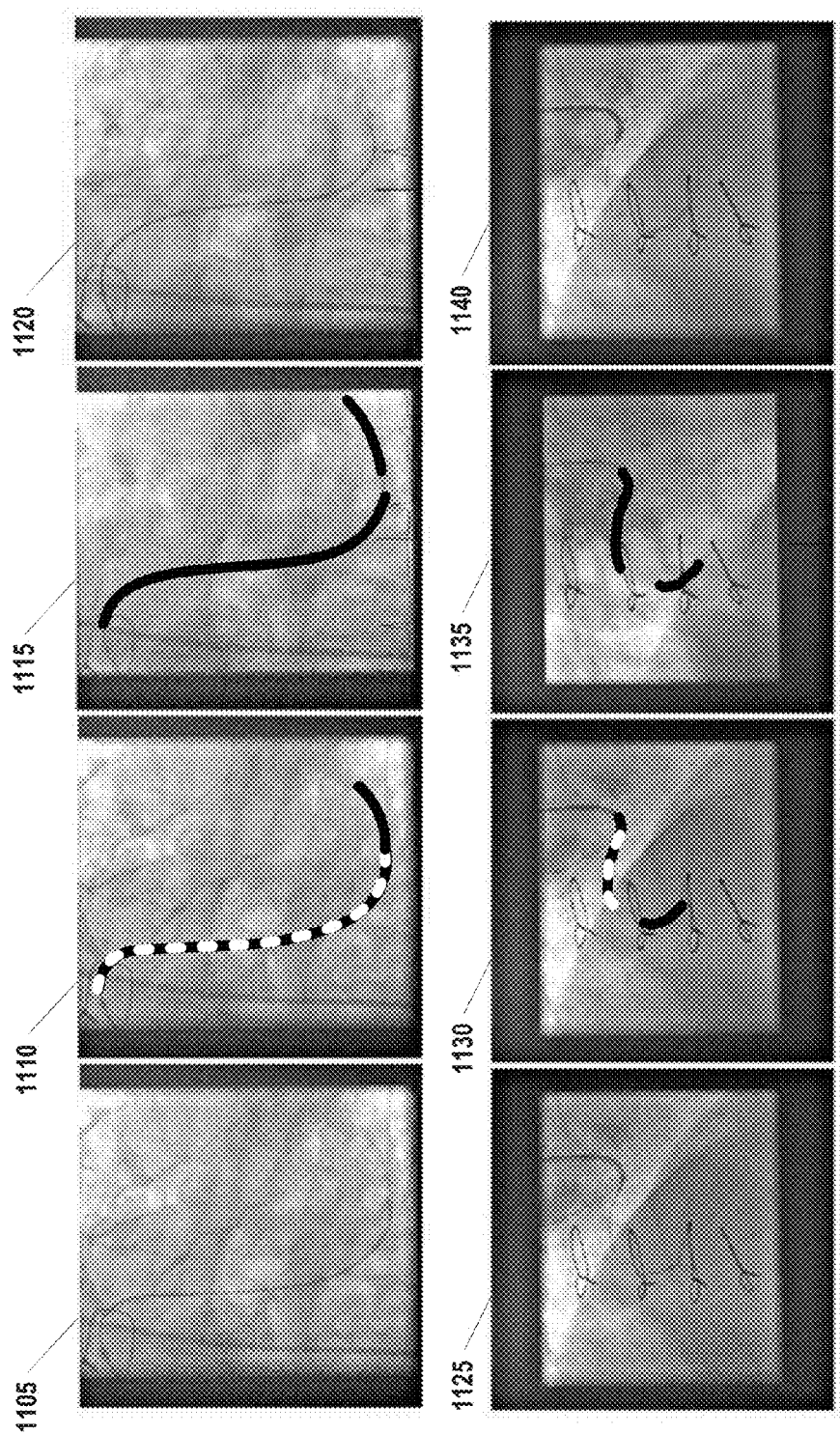
FIG. 11 provides two examples (first and second row) of prediction-based CTO PCI guidance framework using the tracked vessel result.

To illustrate the techniques described herein for vessel tree tracking applications, 15 2D vessel tree angiography videos were used. The frame size is 512×512 pixels and the size of the pixels is about 0.29 mm (with min: 0.216 mm and max: 0.368 mm). The vessel trees were annotated frame by frame as ground truth by an expert. The distance error is 2.26±1.49 mm. FIG. 9 shows the quantitative results (per case) of vessel tree dataset, as generated according to some embodiments. Note that guidewire tracking guidance was not used in this evaluation. FIG. 10 provides examples and comparison of results for vessel tree tracking where a solid white line is used to show the location of the vessel tree, according to some embodiments. The first row includes original images from the video. The second row of images is the ground truth. The third row of images is tracking result without enforcing shape constraint (no binary edge term in Equation 1). Finally, the fourth row is the result acquired using the techniques described herein FIG. 11 provides two examples (first and second row) of prediction-based CTO PCI guidance framework using the tracked vessel result. Images 1105 and 1125 are the original Cine images. Images 1110 and 1130 are Cine tracking results of guidewire (white) and vessel (striped). Images 1115 and 1135 are the predicted vessel in the fluoroscopy images using tracked guidewire and learnt model. Images 1120 and 1140 are the corresponding Cine images to fluoroscopy Images 1115 and 1135 by finding corresponding ECG signal.

The results demonstrate that the techniques described herein are suitable for tracking CTO target vessel. From FIGS. 8 and 10, one can see that incorporating the smoothness shape constraints improves the tracking performance. For example, in videos 3 and 4 in FIG. 8, one can see without shape constraints the landmarks would drift locally thus the whole vessel structure is degenerated. In videos 1 and 2 in FIG. 10, without shape constraints, the vessel trees are degenerated. FIG. 11 shows two examples of the vessel overlay results using the vessel tracking method described herein. It demonstrates that the automated vessel tracking algorithm described herein makes the CTO vessel overlay visualization framework on the fluoroscopy images an automated approach.

Figure 12:
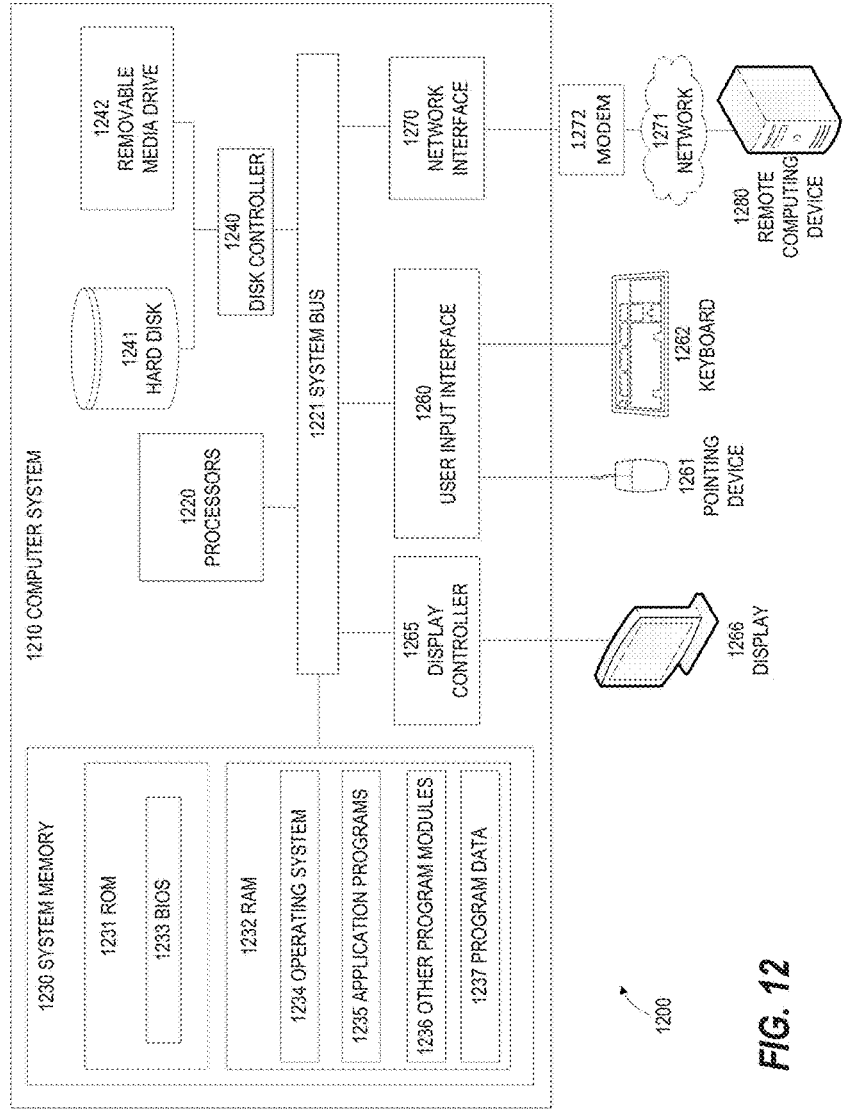
FIG. 12 illustrates an exemplary computing environment within which embodiments of the invention may be implemented.

FIG. 12 illustrates an exemplary computing environment 1200 within which embodiments of the invention may be implemented. For example, this computing environment 1200 may be used to implement one or more of devices shown in FIG. 1 and execute the vessel tracking process described herein. The computing environment 1200 may include computer system 1210, which is one example of a computing system upon which embodiments of the invention may be implemented. Computers and computing environments, such as computer system 1210 and computing environment 1200, are known to those of skill in the art and thus are described briefly here.

As shown in FIG. 12, the computer system 1210 may include a communication mechanism such as a bus 1221 or other communication mechanism for communicating information within the computer system 1210. The computer system 1210 further includes one or more processors 1220 coupled with the bus 1221 for processing the information. The processors 1220 may include one or more central processing units (CPUs), graphical processing units (GPUs), or any other processor known in the art.

The computer system 1210 also includes a system memory 1230 coupled to the bus 1221 for storing information and instructions to be executed by processors 1220. The system memory 1230 may include computer readable storage media in the form of volatile and/or nonvolatile memory, such as read only memory (ROM) 1231 and/or random access memory (RAM) 1232. The system memory RAM 1232 may include other dynamic storage device(s) (e.g., dynamic RAM, static RAM, and synchronous DRAM). The system memory ROM 1231 may include other static storage device(s) (e.g., programmable ROM, erasable PROM, and electrically erasable PROM). In addition, the system memory 1230 may be used for storing temporary variables or other intermediate information during the execution of instructions by the processors 1220. A basic input/output system 1233 (BIOS) containing the basic routines that help to transfer information between elements within computer system 1210, such as during start-up, may be stored in ROM 1231. RAM 1232 may contain data and/or program modules that are immediately accessible to and/or presently being operated on by the processors 1220. System memory 1230 may additionally include, for example, operating system 1234, application programs 1235, other program modules 1236 and program data 1237.

The computer system 1210 also includes a disk controller 1240 coupled to the bus 1221 to control one or more storage devices for storing information and instructions, such as a hard disk 1241 and a removable media drive 1242 (e.g., floppy disk drive, compact disc drive, tape drive, and/or solid state drive). The storage devices may be added to the computer system 1210 using an appropriate device interface (e.g., a small computer system interface (SCSI), integrated device electronics (IDE), Universal Serial Bus (USB), or FireWire).

The computer system 1210 may also include a display controller 1265 coupled to the bus 1221 to control a display 1266, such as a cathode ray tube (CRT) or liquid crystal display (LCD), for displaying information to a computer user. The computer system includes an input interface 1260 and one or more input devices, such as a keyboard 1262 and a pointing device 1261, for interacting with a computer user and providing information to the processor 1220. The pointing device 1261, for example, may be a mouse, a trackball, or a pointing stick for communicating direction information and command selections to the processor 1220 and for controlling cursor movement on the display 1266. The display 1266 may provide a touch screen interface which allows input to supplement or replace the communication of direction information and command selections by the pointing device 1261.

The computer system 1210 may perform a portion or all of the processing steps of embodiments of the invention in response to the processors 1220 executing one or more sequences of one or more instructions contained in a memory, such as the system memory 1230. Such instructions may be read into the system memory 1230 from another computer readable medium, such as a hard disk 1241 or a removable media drive 1242. The hard disk 1241 may contain one or more datastores and data files used by embodiments of the present invention. Datastore contents and data files may be encrypted to improve security. The processors 1220 may also be employed in a multi-processing arrangement to execute the one or more sequences of instructions contained in system memory 1230. In alternative embodiments, hard-wired circuitry may be used in place of or in combination with software instructions. Thus, embodiments are not limited to any specific combination of hardware circuitry and software.

As stated above, the computer system 1210 may include at least one computer readable medium or memory for holding instructions programmed according to embodiments of the invention and for containing data structures, tables, records, or other data described herein. The term "computer readable medium" as used herein refers to any medium that participates in providing instructions to the processor 1220 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 1241 or removable media drive 1242. Non-limiting examples of volatile media include dynamic memory, such as system memory 1230. Non-limiting examples of transmission media include coaxial cables, copper wire, and fiber optics, including the wires that make up the bus 1221. Transmission media may also take the form of acoustic or light waves, such as those generated during radio wave and infrared data communications.

The computing environment 1200 may further include the computer system 1210 operating in a networked environment using logical connections to one or more remote computers, such as remote computer 1280. Remote computer 1280 may be a personal computer (laptop or desktop), a mobile device, a server, a router, a network PC, a peer device or other common network node, and typically includes many or all of the elements described above relative to computer system 1210. When used in a networking environment, computer system 1210 may include modem 1272 for establishing communications over a network 1271, such as the Internet. Modem 1272 may be connected to bus 1221 via user network interface 1270, or via another appropriate mechanism.

Network 1271 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 1210 and other computers (e.g., remote computer 1280). The network 1271 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 1271.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for."

We claim:

1. A method for tracking vessels in image data, the method comprising:
   receiving a plurality of image frames;
   annotating a target vessel in the plurality of image frames;
   selecting a plurality of tracking targets associated with the target vessel based on a first image frame included in the plurality of image frames;
   for each respective image frame, determining a set of tracking points according to a tracking algorithm comprising:
      selecting a plurality of landmark hypothesis points for each tracking target in the respective frame based on a comparison with a previous image frame,
      constructing a directed acyclic graph from the plurality of landmark hypothesis points, and
      solving the directed acyclic graph to yield a plurality of optimal landmarks for the respective image frame;
   wherein the plurality of landmark hypothesis points for each tracking target in the respective image frame is determined by generating a unary score for each node in the directed acyclic graph based on the respective image frame and the previous image frame.

2. The method of claim 1, further comprising:
   for each respective image frame, performing a presentation process comprising:
      presenting the respective image frame on a display,
      overlaying a visual indication of the target vessel on the respective image frame on the display based on the plurality of optimal landmarks associated with the respective image frame.

3. The method of claim 2, wherein the visual indication of the target vessel is a colored line.

4. The method of claim 1, wherein the unary score for each node is generated based on one or more of a local intensity similarity, Frangi vesselness response, and a location constraint.

5. The method of claim 1, wherein the tracking algorithm further comprises:
   determining a plurality of guidewire points corresponding to a location of a guidewire in the respective image frame; and
   adjusting the unary score for each node based on the plurality of guidewire points.

6. The method of claim 1, wherein the plurality of image frames is 2D fluoroscopy images received from an X-Ray imaging device.

7. The method of claim 1, wherein the target vessel is annotated based on user input.

8. The method of claim 1, wherein the target vessel is annotated using an automated vessel segmentation process.

9. A method for tracking vessels in image data, the method comprising:
   selecting a plurality of landmark hypothesis points corresponding to a target vessel included in an image frame included in a Cine video;
   constructing a graph comprising a plurality of nodes, each node corresponding to one or more of the plurality of landmark hypothesis points;
   solving the graph to identify a plurality of optimal landmarks corresponding to the target vessel;
   generating a graphical indication of the target vessel based on the plurality of optimal landmarks; and
   presenting the image frame on display with the graphical indication of the target vessel overlaying the image frame;
   determining a unary score for each of the plurality of nodes based on the comparison of the image frame and the immediately preceding imaging frame in the Cine video, wherein the graph is solved based on the unary score determined for each of the plurality of nodes.

10. The method of claim 9, wherein the graph is a directed acyclic graph.

11. The method of claim 9,
   wherein the plurality of landmark hypothesis points corresponding to the target vessel included in the image frame are selected based on the unary score determined for each of the plurality of nodes.

12. The method of claim 11, further comprising:
determining a plurality of guidewire points corresponding to a location of a guidewire in the image frame; and
adjusting the unary score for each node in the graph based on the plurality of guidewire points.

13. The method of claim 9, further comprising:
determining a binary score for each graph edge included in the graph, each respective binary score enforcing a structural constraint determined based on the comparison of the image frame and the immediately preceding imaging frame in the Cine video,
wherein the graph is further solved based on the binary score determined for each of the plurality of nodes.

14. A system for tracking vessels in image data, the system comprising:
an imaging computer configured to execute a plurality of components comprising:
an annotation component configured to annotate a target vessel in a plurality of image frames,
a landmark selection component configured to select a plurality of tracking targets associated with the target vessel based on a first frame included in the plurality of image frames,
a hypothesis generation component configured to select a plurality of landmark hypothesis points for each tracking target in the each of the plurality of image frames,
a graph construction component configured to construct a directed acyclic graph from the plurality of landmark hypothesis points, and
a graph solving component configured to solve the directed acyclic graph to yield a plurality of optimal landmarks for each respective image frame in the plurality of image frames;
a display configured to:
present each respective image frame included in the plurality of image frames, and
overlay a visual indication of the target vessel on each respective image frame in the plurality of image frames based on the plurality of optimal landmarks associated with the respective image frame; and
a guidewire tracking component configured to track a location of a guidewire, wherein the plurality of landmark hypothesis points is selected based on the location of the guidewire related to the target vessel.

15. The system of claim 14, further comprising:
an X-Ray imaging device configured to acquire the plurality of image frames.

* * * * *